United States Patent
Bernstein et al.

(10) Patent No.: US 10,004,512 B2
(45) Date of Patent: Jun. 26, 2018

(54) OCCLUSION DEVICE AND METHOD OF USE THEREOF

(71) Applicant: COOK BIOTECH INCORPORATED, West Lafayette, IN (US)

(72) Inventors: Ryan Bernstein, San Francisco, CA (US); Jeremy Metz, Whitestown, IN (US); Bhavin Shah, West Lafayette, IN (US)

(73) Assignee: COOK BIOTECH INCORPORATED, West Lafayette, IN (US)

( * ) Notice: Subject to any disclaimer, the term of this patent is extended or adjusted under 35 U.S.C. 154(b) by 171 days.

(21) Appl. No.: 14/605,296

(22) Filed: Jan. 26, 2015

(65) Prior Publication Data

US 2015/0209049 A1    Jul. 30, 2015

Related U.S. Application Data

(60) Provisional application No. 61/932,903, filed on Jan. 29, 2014.

(51) Int. Cl.
*A61M 29/00* (2006.01)
*A61B 17/12* (2006.01)

(52) U.S. Cl.
CPC .. *A61B 17/12136* (2013.01); *A61B 17/12109* (2013.01); *A61B 2017/1205* (2013.01)

(58) Field of Classification Search
CPC ........ A61B 17/12109; A61B 17/12136; A61B 2017/1205

USPC ................. 128/830, 831, 835–837, 839, 841
See application file for complete search history.

(56) References Cited

U.S. PATENT DOCUMENTS

| | | | |
|---|---|---|---|
| 4,425,908 A * | 1/1984 | Simon | A61F 2/01 128/899 |
| 4,441,495 A | 4/1984 | Hicswa | |
| 4,517,979 A | 5/1985 | Pecenka | |
| 4,545,367 A | 10/1985 | Tucci | |
| 4,832,055 A * | 5/1989 | Palestrant | A61F 2/01 128/899 |
| 5,181,921 A | 1/1993 | Makita | |
| 5,634,942 A * | 6/1997 | Chevillon | A61F 2/01 606/194 |
| 5,653,690 A | 8/1997 | Booth et al. | |
| 5,669,933 A * | 9/1997 | Simon | A61F 2/01 600/191 |
| 5,779,672 A | 7/1998 | Dormandy | |

(Continued)

FOREIGN PATENT DOCUMENTS

| WO | WO1999/012484 | 3/1999 |
|---|---|---|
| WO | WO2010/116074 | 10/2010 |

*Primary Examiner* — Son Dang

(74) *Attorney, Agent, or Firm* — Brinks Gilson & Lione

(57) ABSTRACT

One aspect of the present invention provides a device for occluding a body cavity. In one embodiment, the occlusion device includes include a hub extending from an upstream end to a downstream end and along a central axis. A number of struts are attached to the upstream end and extend upstream from the hub. An expandable balloon is attached to the downstream end and extending downstream from the hub. Another aspect of the present invention provides a method for occluding fluid flow within in a body cavity including placing an occlusion device within the body cavity.

12 Claims, 4 Drawing Sheets

(56) References Cited

U.S. PATENT DOCUMENTS

| | | | |
|---|---|---|---|
| 5,853,422 A * | 12/1998 | Huebsch | A61B 17/0057 606/157 |
| 5,855,565 A * | 1/1999 | Bar-Cohen | A61M 29/02 604/104 |
| 6,231,589 B1 * | 5/2001 | Wessman | A61F 2/01 606/200 |
| 6,331,183 B1 * | 12/2001 | Suon | A61F 2/01 606/200 |
| 6,346,116 B1 * | 2/2002 | Brooks | A61F 2/01 606/159 |
| 6,379,329 B1 | 4/2002 | Naglreiter et al. | |
| 6,383,205 B1 * | 5/2002 | Samson | A61B 17/221 606/200 |
| 6,447,530 B1 * | 9/2002 | Ostrovsky | A61F 2/01 606/108 |
| 6,517,559 B1 * | 2/2003 | O'Connell | A61F 2/01 606/108 |
| 6,547,804 B2 | 4/2003 | Porter et al. | |
| 6,663,589 B1 | 12/2003 | Halevy | |
| 6,964,673 B2 * | 11/2005 | Tsugita | A61F 2/01 606/200 |
| 6,972,025 B2 * | 12/2005 | WasDyke | A61F 2/01 606/200 |
| 7,252,650 B1 * | 8/2007 | Andrews | A61F 2/958 604/103.06 |
| 7,713,282 B2 * | 5/2010 | Frazier | A61B 17/0057 606/200 |
| 7,935,075 B2 * | 5/2011 | Tockman | A61N 1/057 600/109 |
| 8,029,534 B2 * | 10/2011 | Hruska | A61B 17/0057 606/213 |
| 8,057,539 B2 * | 11/2011 | Ghione | A61F 2/2436 623/2.11 |
| 8,152,831 B2 * | 4/2012 | Magnuson | A61F 2/013 606/200 |
| 8,182,508 B2 * | 5/2012 | Magnuson | A61F 2/013 606/200 |
| 8,603,127 B2 * | 12/2013 | Alferness | A61B 17/12022 128/200.24 |
| 8,920,458 B2 * | 12/2014 | McGuckin, Jr. | A61F 2/01 606/200 |
| 8,956,319 B2 * | 2/2015 | Dillard | A61B 17/12104 604/8 |
| 8,974,527 B2 * | 3/2015 | Gonzalez | A61B 17/12022 623/9 |
| 9,220,522 B2 * | 12/2015 | Fulkerson | A61B 17/221 |
| 9,326,759 B2 * | 5/2016 | Chanduszko | A61B 17/0057 |
| 9,408,620 B2 * | 8/2016 | Rosenbluth | A61B 17/320725 |
| 9,445,829 B2 * | 9/2016 | Brady | A61B 17/12109 |
| 9,456,834 B2 * | 10/2016 | Folk | A61F 2/013 |
| 9,510,929 B2 * | 12/2016 | McGuckin, Jr. | A61F 2/01 |
| 9,592,107 B2 * | 3/2017 | Molgaard-Nielsen | A61F 2/01 |
| 9,713,549 B2 * | 7/2017 | Callister | A61F 6/22 |
| 9,827,101 B2 * | 11/2017 | Solem | A61F 2/246 |
| 9,833,304 B2 * | 12/2017 | Horan | A61F 2/01 |
| 2001/0037129 A1 * | 11/2001 | Thill | A61B 17/0057 606/213 |
| 2002/0022860 A1 | 2/2002 | Borillo et al. | |
| 2002/0095174 A1 * | 7/2002 | Tsugita | A61F 2/01 606/200 |
| 2002/0128679 A1 * | 9/2002 | Turovskiy | A61F 2/013 606/200 |
| 2002/0128681 A1 * | 9/2002 | Broome | A61F 2/013 606/200 |
| 2002/0138094 A1 * | 9/2002 | Borillo | A61F 2/013 606/200 |
| 2003/0171771 A1 * | 9/2003 | Anderson | A61B 17/12172 606/200 |
| 2003/0220667 A1 * | 11/2003 | van der Burg | A61B 17/0057 606/200 |
| 2004/0093017 A1 * | 5/2004 | Chanduszko | A61B 17/0057 606/200 |
| 2004/0098031 A1 * | 5/2004 | van der Burg | A61B 17/0057 606/200 |
| 2004/0153117 A1 * | 8/2004 | Clubb | A61F 2/01 606/200 |
| 2004/0176799 A1 * | 9/2004 | Chanduszko | A61B 17/0057 606/213 |
| 2005/0043757 A1 * | 2/2005 | Arad | A61B 17/0401 606/200 |
| 2005/0065548 A1 * | 3/2005 | Marino | A61B 17/0057 606/213 |
| 2005/0085844 A1 * | 4/2005 | Tremulis | A61B 17/12022 606/193 |
| 2005/0113861 A1 * | 5/2005 | Corcoran | A61B 17/0057 606/200 |
| 2006/0052814 A1 | 3/2006 | Sater | |
| 2006/0058833 A1 * | 3/2006 | VanCamp | A61B 17/12022 606/200 |
| 2006/0241745 A1 * | 10/2006 | Solem | A61F 2/2418 623/2.18 |
| 2007/0060943 A1 * | 3/2007 | Dorn | A61F 2/95 606/200 |
| 2007/0167974 A1 * | 7/2007 | Cully | A61B 17/221 606/200 |
| 2007/0173885 A1 * | 7/2007 | Cartier | A61F 2/01 606/200 |
| 2007/0179527 A1 * | 8/2007 | Eskuri | A61B 17/0057 606/213 |
| 2008/0183203 A1 * | 7/2008 | Fitzgerald | A61B 17/12022 606/194 |
| 2008/0188887 A1 * | 8/2008 | Batiste | A61F 2/01 606/200 |
| 2008/0221609 A1 * | 9/2008 | McGuckin | A61F 2/01 606/200 |
| 2008/0249562 A1 * | 10/2008 | Cahill | A61B 17/0057 606/215 |
| 2009/0005803 A1 * | 1/2009 | Batiste | A61F 2/01 606/200 |
| 2009/0062838 A1 | 3/2009 | Brumleve et al. | |
| 2009/0234318 A1 * | 9/2009 | Loulmet | A61B 17/00234 604/500 |
| 2010/0106178 A1 * | 4/2010 | Obermiller | A61B 17/0057 606/194 |
| 2010/0262071 A1 * | 10/2010 | Kutsko | A61B 17/12022 604/30 |
| 2011/0202086 A1 * | 8/2011 | Bates | A61F 2/01 606/200 |
| 2012/0310269 A1 | 12/2012 | Fearnot et al. | |
| 2014/0243873 A1 * | 8/2014 | Franklin | A61M 25/1011 606/194 |
| 2014/0371842 A1 * | 12/2014 | Marquez | A61F 2/2445 623/2.11 |
| 2015/0250497 A1 * | 9/2015 | Marks | A61B 17/221 606/159 |
| 2017/0128185 A1 * | 5/2017 | Molgaard-Nielsen | A61F 2/01 |

* cited by examiner

OCCLUSION DEVICE AND METHOD OF USE THEREOF

RELATED APPLICATIONS

This patent application claims the benefit of U.S. provisional patent application No. 61/932,903, filed Jan. 29, 2014, the entire contents of which application is hereby incorporated by reference.

FIELD OF THE INVENTION

The present invention relates generally to medical devices for use in occluding a body cavity and to methods of using such devices.

BACKGROUND

There are a number of reasons why it may be desirable to occlude a body cavity. For example, the site of a stroke or other vascular accident can be treated by placing an occlusion device proximal of the site to block the flow of blood to the site, thereby alleviating leakage at the site. An aneurysm can be treated by the introduction of an occlusion device through the neck of the aneurysm. Tumors can be treated by occluding the flow of blood to a target site of interest.

A number of different devices may be used to occlude a body cavity, such as a blood vessel. One example of such an occlusion device is an embolization coil. Embolization coils are permanent and promote blood clots or tissue growth over a period of time, thereby occluding the body cavity. However, while the blood clots or the tissue grow, blood may continue to flow past the coil and through the body cavity. It may take a significant period of time for sufficient tissue to grow to fully occlude the body cavity. This leaves a patient open to a risk of injury from the condition which requires the body cavity be occluded.

Other occlusion devices include a coil having fibers, threads or strands attached to the coil. Such occlusion devices act to block the flow of blood through a vessel by the formation of an embolus in the vessel. However, while these occlusion devices can provide effective occlusion, they too suffer from the disadvantage that blood flow continues until the embolus has been formed, thus requiring additional time before effective occlusion is obtained.

Plug-style occlusion devices have also been developed. While these devices are intended to provide a physical barrier to blood flow, and thereby stop blood flow more quickly, known devices are generally bulky and often require thrombosis to obtain reliable occlusion.

SUMMARY

One aspect of the present invention provides a device for occluding a body cavity having a fluid flow from an upstream region to a downstream region. One embodiment of the occlusion device includes a hub extending from an upstream hub end to a downstream hub end and along a central axis. A number of struts are attached to the upstream end and extend upstream from the hub. An expandable balloon is attached to the downstream end of the hub and extends downstream from the hub. In one embodiment, the struts are movable from a closed configuration where the struts extend substantially along the central axis to an open configuration where the struts extend radially away from the central axis.

The expandable balloon can be an open balloon having an open upstream end attached to the hub and a closed downstream end. In certain embodiments, the open upstream end of the expandable balloon is attached to the hub by a number of attachment lines. In other embodiments, the expandable balloon is a closed inflatable balloon having an inflation valve near the downstream end. The expandable balloon can have a number of barbs positioned on the outside surface of the balloon. The barbs can act to prevent migration of the inflated balloon when it is positioned within the cavity so as to occlude the cavity.

Another aspect of the present invention provides a method for occluding fluid flow within in a body cavity. The method includes positioning an occluding device as described above within the body cavity and moving the struts from a closed configuration where the struts extend substantially along the central axis to an open configuration where the struts extend radially away from the central axis and where an upstream end of a least one of the struts contacts a wall of the cavity. The expandable balloon is inflated to contact the wall of the body cavity so that the cavity is occluded and fluid flow eliminated.

BRIEF DESCRIPTION OF THE DRAWINGS

The invention may be more fully understood by reading the following description in conjunction with the drawings, in which.

DEFINITIONS

Figure 1:
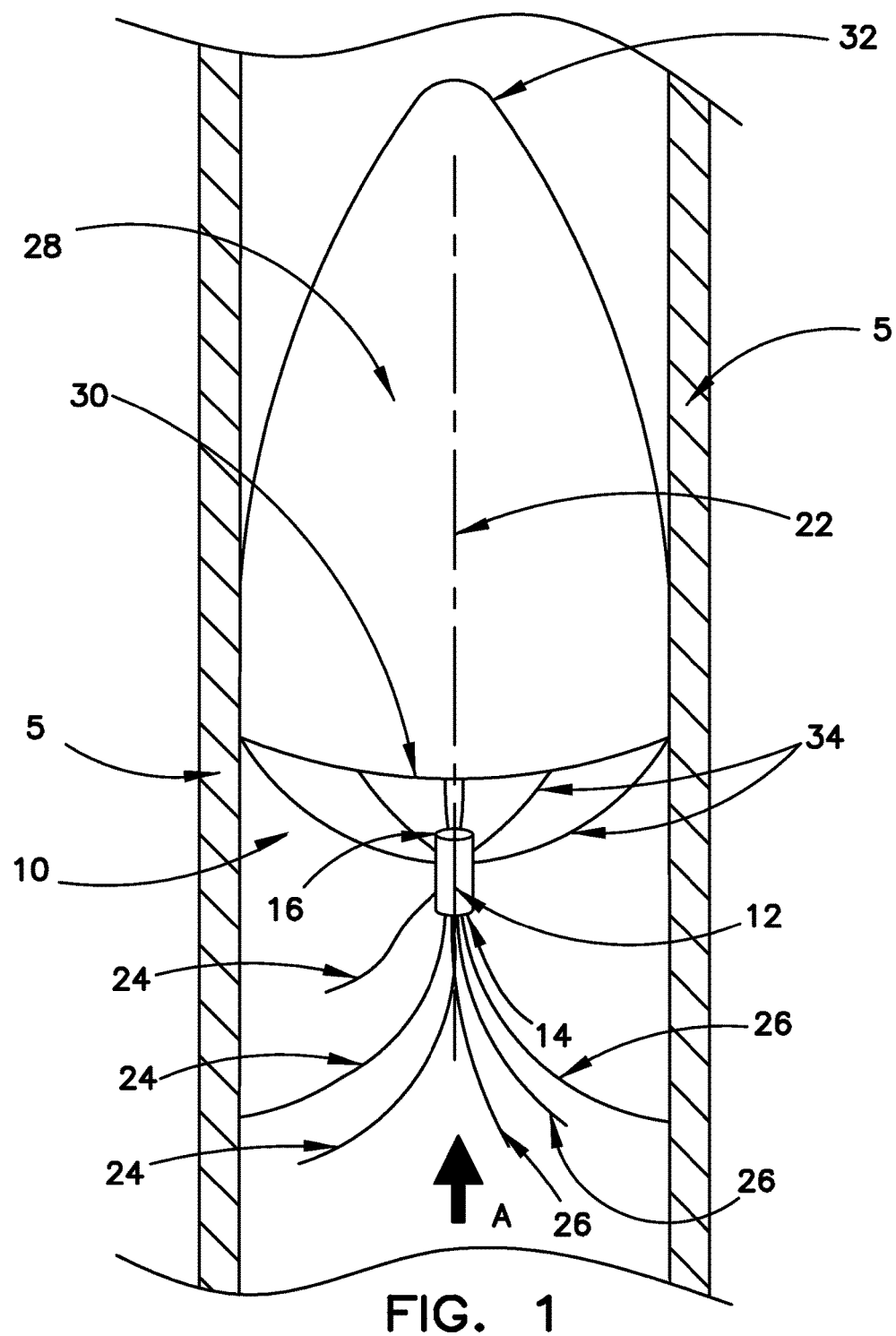
FIG. 1 is a side view illustrating one embodiment of an occluding device in an expanded configuration.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

For the purposes of describing the present embodiments, the term "upstream" refers to the region of a body cavity from which fluid flows. The term "downstream" refers to the region of the body cavity to which fluid flows. For example, where the body cavity is a blood vessel, blood will flow from the upstream region to the downstream region of the blood vessel. When referring to components or parts of the occluding devices disclosed herein, the term "upstream end" refers to the end positioned closest to the upstream region of the body cavity and the term "downstream end" refers to the end closest to the downstream region of the body cavity.

For the purposes of describing the present embodiments, the term "occluding" of a vessel includes any blocking that prevents or inhibits fluid flow through the vessel.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Devices for Occluding a Body Cavity

One aspect of the present invention provides a medical device for occluding a body cavity and at least limiting fluid flow through the body cavity. In a preferred embodiment, the body cavity is totally occluded resulting in the elimination of fluid flow. In certain embodiments, the body cavity is a vessel of the vascular system of the human or veterinary subject.

Referring now to FIG. 1, one embodiment of an occlusion device 10 embodying the principles of the present invention is illustrated. FIG. 1 shows the occlusion device in an expanded configuration. The device is implanted within a body cavity having a cavity wall 5 so as to occlude the body cavity and at least partially prevent fluid flow from an upstream region to a downstream region, i.e. to restrict or prevent fluid flow in the direction shown by arrow "A."

The occlusion device 10 includes a first hub 12 extending from an upstream end 14 to a downstream end 16 along a central axis 22. A plurality of struts 24 attach to the hub 12 and extend upstream and diverge to contact the cavity wall. In certain embodiments, struts 24 terminate in anchoring mechanisms 26 which engage the cavity wall, when in an expanded configuration, and act to prevent migration of occlusion device 10 within the body cavity. While the exact number of struts 24 may vary depending on the needs of a particular application, the present example illustrates six struts. In other embodiments, the occlusion device includes 3, 4, 5, 7, 8, 9 or more struts.

Balloon 28 attaches to hub 12 and, when deployed as illustrated in FIG. 1, extends downstream from hub 12. In the embodiment illustrated in FIG. 1, balloon 28 is a "wind sock" shaped balloon having an open upstream end 30 attached to hub 12 and a tapered closed downstream end 32. In certain embodiments, open upstream end 30 is attached to hub 12 by a plurality of attachment lines 34. Balloon 32 can be inflated as a result of flow of fluid in direction "A" resulting in fluid entering open upstream end 30 and causing inflation of the balloon. In other embodiments, balloon 28 can be a cylindrical balloon having an open (upstream) end and a closed (downstream) end.

In various embodiments, balloon 28 is shaped and sized to contact and press against cavity wall 5 when inflated and thereby occlude the cavity resulting in an obstruction to fluid flow. Such a balloon may be formed of any flexible material, such as a nylon, polyolefin, polyamide, polyester, polyurethane, fluoropolymer, polyethylene, polytetrafluoroethylene (PTFE), polyethyleneterepthalate (PET), polyvinyl chloride, latex, natural rubber, synthetic rubber, elastomer, silicone and mixtures and/or copolymers of two or more of these materials.

In one embodiment, the thickness of the wall of the balloon is approximately 0.0005 inch thick. However, the wall of the balloon can be of any appropriate thickness provided that the thickness does not compromise properties that are important for achieving optimum performance. In various embodiments, the balloon wall thickness is within the range of approximatel 0.0005 inch to 0.0012 inch thick.

Struts 24 can be manufactured from one or more suitable biocompatible materials such as stainless steel, nickel titanium alloy, nitinol, MP35N, gold, tantalum, platinum or platinum iridium, niobium, tungsten, inconel, ceramic, nickel, titanium, stainless steel/titanium composite, cobalt, chromium, cobalt/chromium alloys, magnesium, aluminum, or other biocompatible metals and/or composites or alloys such as carbon or carbon fiber. Other materials that can be used in the manufacture of the struts include cellulose acetate, cellulose nitrate, cross-linked polyvinyl alcohol (PVA) hydrogel, cross-linked PVA hydrogel foam, polyurethane, styrene isobutylene-styrene block copolymer (Kraton), polyethylene terephthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof. In certain preferred embodiments, the struts include stainless steel, cobalt-chromium or a nickel-titanium alloy (for example NITINOL).

Anchoring mechanisms 26 can be, for example, hooks or burbs attached to the ends of struts 24. In certain embodiments, anchoring mechanisms 26 are formed by bending the ends of struts 24 so that the ends point downstream and into the cavity wall. In such embodiments, force extended on the device in a downstream direction, for example by fluid pressure against the inner wall of balloon 28, acts to push the anchoring mechanisms into the cavity wall, hence limiting any movement of the device.

Figure 2:
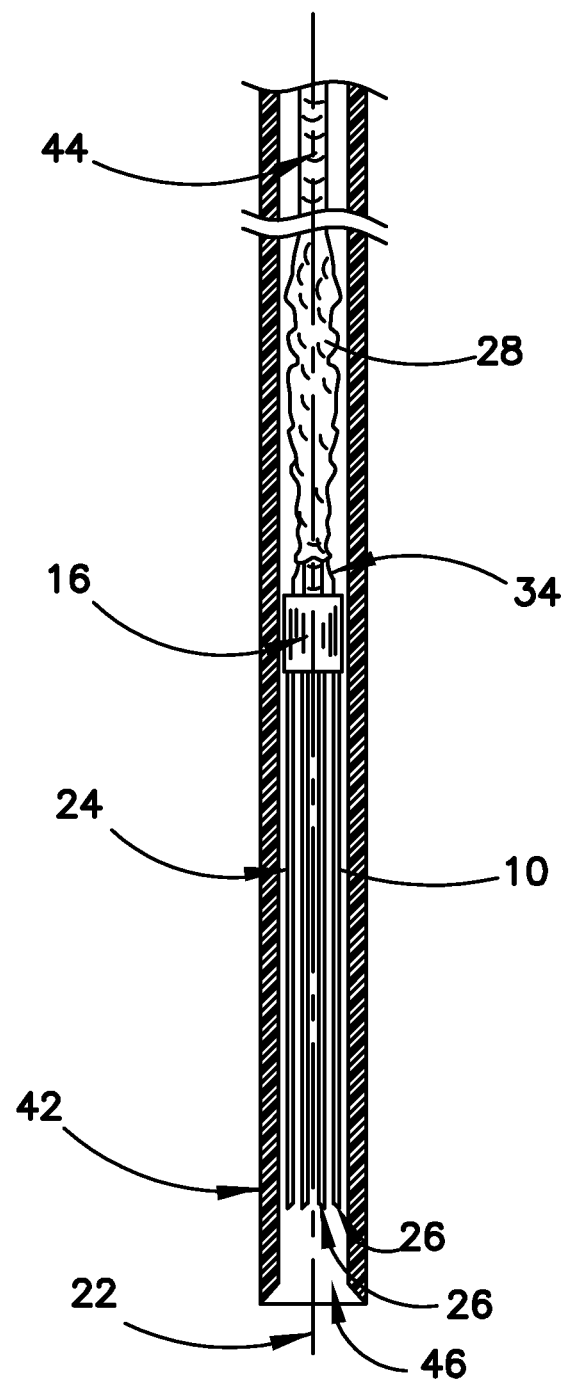
FIG. 2 is a side view illustrating the embodiment of FIG. 1 in a compressed configuration.

FIG. 2 illustrates occlusion device 10 in a collapsed configuration. Here, the occlusion device 10 is shown positioned within the lumen of delivery catheter 42 for delivery to the body cavity. In this configuration, delivery catheter constrains struts 24 in a closed configuration where the struts extend substantially along central axis 22. Balloon 28 is present in a deflated configuration and is positioned behind hub 12. In certain embodiments, pusher mechanism 44 extends along the lumen of catheter 42 from a proximal end to occlusion device 10. In one embodiment, pusher mechanism 44 extends to hub 16. Here, balloon 28 can be disposed around pusher mechanism 44 within the lumen of catheter 42 for delivery to the body cavity.

Pusher mechanism 44 can be used to push occlusion device 10 out of end 46 of catheter 42. Struts 24 diverge to contact the cavity wall 5 and anchor occlusion device 10 when they are no longer constrained by catheter 42. As balloon 28 exits through end 46 of catheter 42, it becomes inflated by fluid flow in the direction of arrow "A" so that the perimeter of open end 30 contacts and is pushed against the wall of the body cavity, resulting in the occlusion of the body cavity and the elimination of fluid flow.

Attachment lines 34 attach the perimeter of open end 30 of balloon 28 to hub 16. These lines can be formed from sutures or any other suitable material. In one embodiment, at least some of attachment lines 34 are formed to diverge towards the cavity wall when no longer restrained by catheter 42. For example, these attachment lines can be spring loaded or formed from a super-elastic nickel-titanium alloy, such as NITINOL. Divergence of the attachment lines causes at least a partial opening of balloon 28 and inflow of fluid into the balloon. This, in turn, results in further inflation of the balloon. In other embodiments, at least a portion of the perimeter of open end 30 of balloon 28 includes a stiffened region that unfolds from a folds configuration to assist in the inflation of the balloon when it is released from catheter 42. For example, a portion of the perimeter may be thickened or may include spring loaded material or a super-elastic nickel-titanium alloy.

Figure 3:
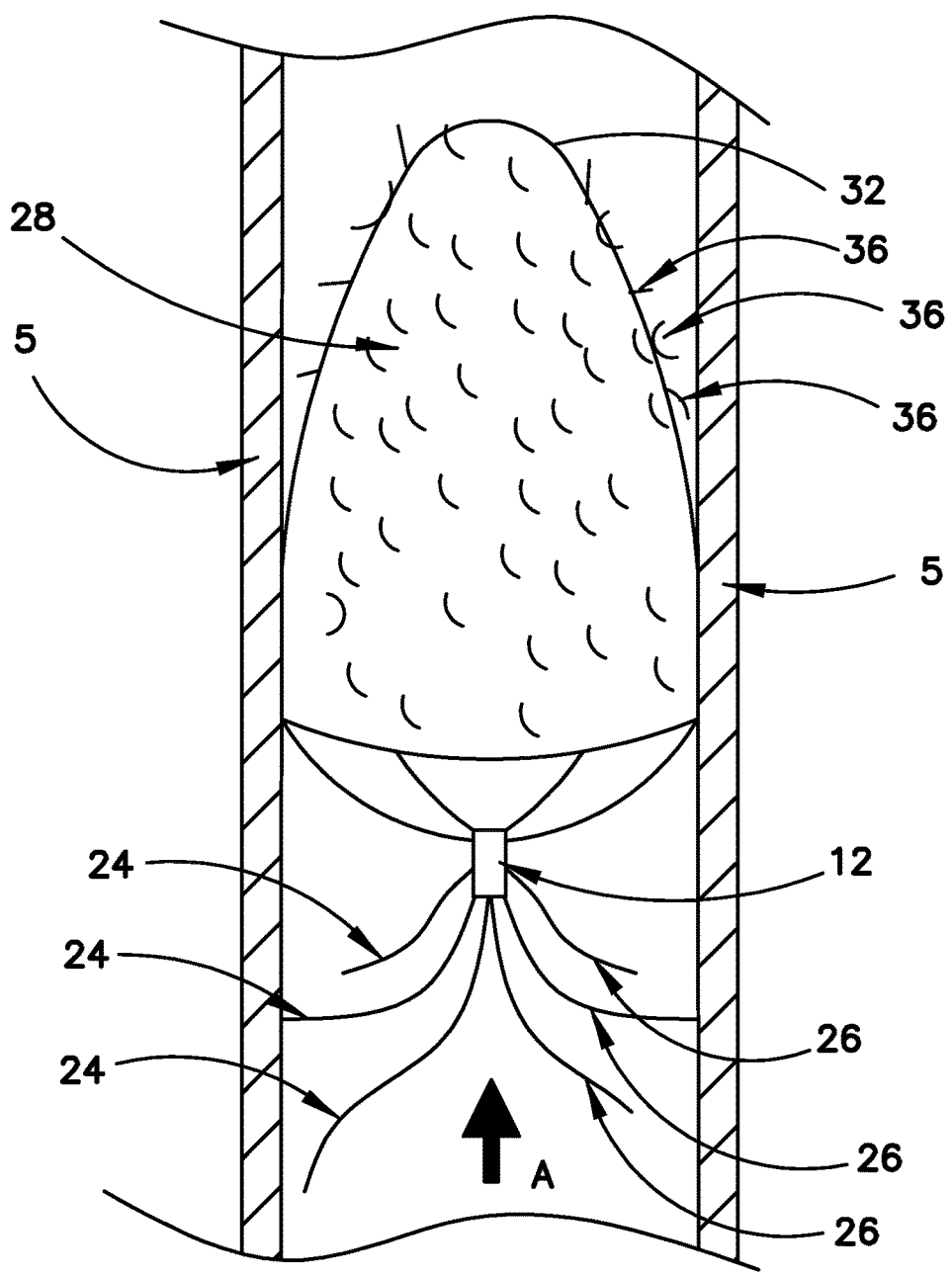
FIG. 3 is a side view illustrating another embodiment of an occluding device in an expanded configuration.

Turning now to FIG. 3, this figure illustrates another embodiment of an occluding device. Here, open ended balloon 28 includes an outer surface providing for enhanced attachment to the cavity wall 5. Such attachment provides additional stability for the device by acting to prevent migration of the device when implanted. For example, the outer surface may include micro-barbs 36. In certain embodiments, micro-barbs 36 for formed from a polymeric or metallic material partially implanted within the balloon wall. In some embodiments, the micro-barbs are positioned so that they extend from the balloon surface in a downstream direction and tend to penetrate cavity wall 5 and counteract any tendency for the balloon to migrate downstream. In other embodiments, the balloon wall is formed having a roughened or textured outer surface providing increased friction between the balloon wall and the cavity wall.

Figure 4:
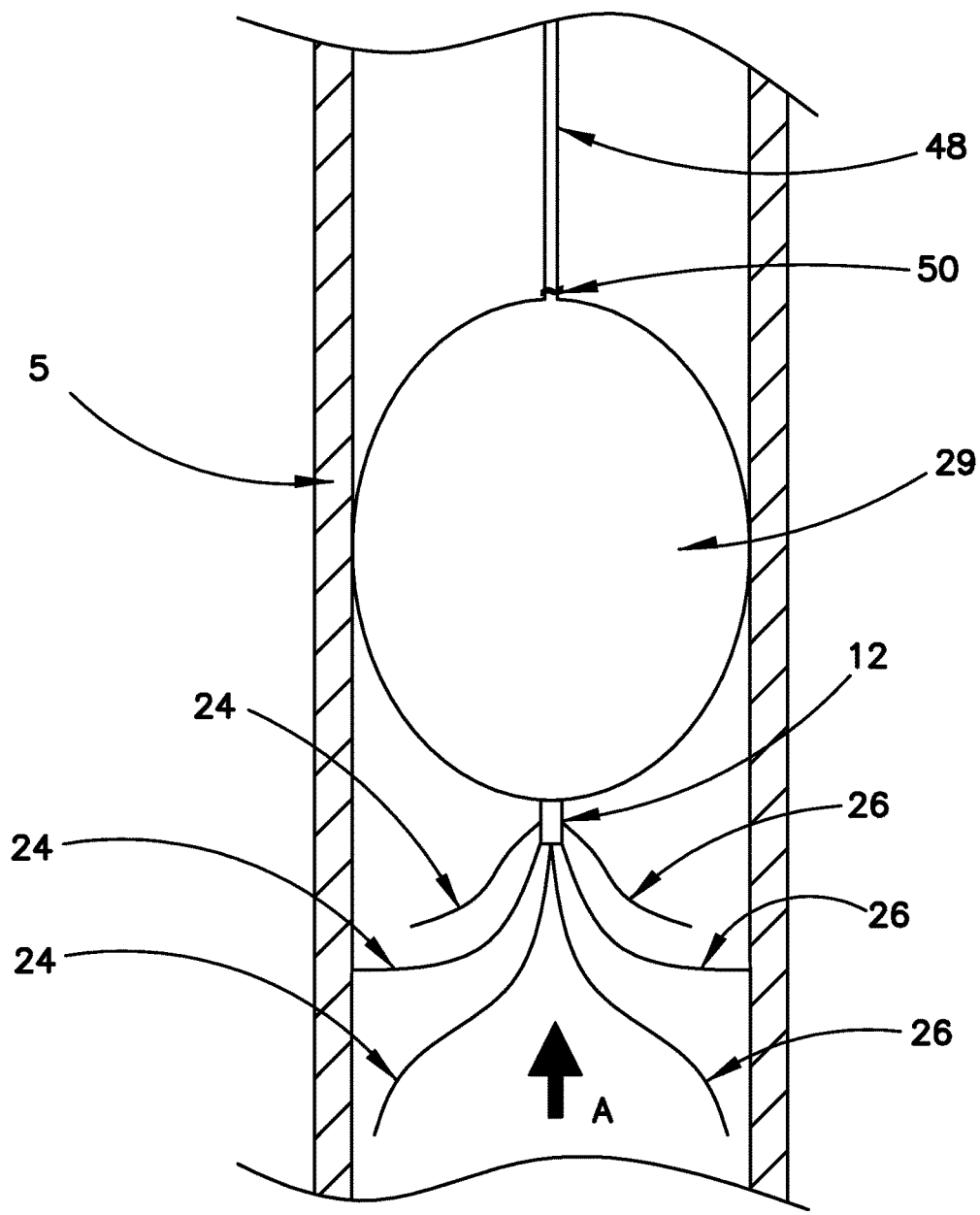
FIG. 4 is a side view illustrating yet another embodiment of an occluding device in an expanded configuration

FIG. 4 illustrates an expended configuration of yet another embodiment of an occlusion device. This embodiment again includes a hub 12 and a plurality of struts 24 attached to hub 12 and extending upstream and diverging to contact the cavity wall 5. Struts 24 can again terminate in anchoring mechanisms 26 which act to prevent migration of the occlusion device within the body cavity.

Balloon 29 attaches to hub 12 and extends downstream from hub 12. In the embodiment illustrated in FIG. 4, balloon 29 is a closed inflatable balloon having an inflation valve 50 positioned near the downstream end of the balloon. Inflation catheter 48 attaches to inflation valve 50. In some embodiments, inflation catheter can be detached from the occlusion device after balloon 29 is fully inflated and inflation valve 50 closed. Balloon 29 can be attached directly to the downstream end of hub 12, as illustrated in FIG. 4 or, alternatively, can be attached to hub 12 by attachment lines in a manner similar to the embodiment illustrated in FIGS. 1 and 2.

Balloon 29 can be of any shape that occludes the body cavity when the balloon is inflated. For example, balloon 29 can be a round or oval shaped balloon. Alternatively, balloon can be a cylindrical balloon having rounded or flattened end walls. The outer surface of balloon may include micro-barbs and/or be roughened to resist migration of the balloon when implanted. Inflation valve 50 can be configured to close by twisting a guide wire. Such a mechanism may also be used to detach inflation lumen 48 after the balloon is inflated and inflation valve 50 is closed.

Methods for Occluding a Body Cavity

Another aspect of the present invention provides method for occluding a body cavity and at least limiting fluid flow through the body cavity. In a preferred embodiment, the body cavity is a blood vessel of a human or veterinary subject. For example, the method may be used to treat the subject by occluding a blood vessel having a weakened vessel wall or aneurysm. The vessel may be, for example, a cerebral vessel, a renal vessel, or an aortic or a peripheral vascular vessel.

One embodiment of a method of occluding a body cavity will now be illustrated with reference to the occluding device illustrated in FIGS. 1 and 2. However, the general principles of the method are applicable to the other embodiments of the occluding devices disclosed herein.

The occluding device is typically delivered to the site to be occluded by a percutaneous medical procedure. Access into the femoral artery in the leg (or, less commonly, into the radial artery or brachial artery in the arm) is created by an introducer needle. Once access into the artery is gained, a sheath introducer is placed in the opening to keep the artery open and control bleeding. A guiding catheter is pushed through the inducer and advanced to position the tip of the guiding catheter in the site to be occluded.

A guidewire is then inserted through the guiding catheter and advanced to the site to be occluded. When the guidewire is in place, the tip of a catheter having an occlusion device positioned inside, as illustrated in FIG. 2, is inserted at the back of the guidewire and pushed forward until the occlusion device is positioned at the site to be occluded. The catheter is inserted to position open end 46 facing upstream with respect to the flow of fluid (blood) in the body cavity. Pusher mechanism 44 is activated to push the occlusion device out of catheter 42 through open end 46.

As struts 24 move outside of catheter 42, they are no longer constrained by the catheter wall and are free to diverge and move towards the cavity wall. Eventually, hub 16 exits catheter 42 and struts 24 diverge fully and contact and press against the cavity wall. Next, the upstream end 30 of windsock balloon 28 exits catheter 42. Fluid flow within the cavity will tend to delivery fluid though open end 30 and into the interior of balloon 28, causing the balloon to start to inflate.

If attachment lines 34 are formed from a spring-loaded material, such as stainless steel or a super-elastic nickel-titanium alloy, they may be configured to diverge towards the cavity wall when released from catheter 42, assisting in the opening of the upstream end 30 of balloon 28 and inflation of the balloon. Alternatively, stiffened portions of the perimeter of the open end may straighten when released, again resulting in the opening of upstream end 30. Eventually, balloon 28 is fully inflated to inflow of fluid and contacts and presses against the cavity wall, resulting in occlusion of the cavity and elimination of fluid flow. Catheter 42 can then be removed from the vessel.

A similar delivery technique can be used to deliver the occlusion device illustrated in FIG. 4. However, here inflation of balloon 29 does not depend upon flow of fluid within the cavity. Balloon 29 is instead inflated by delivery of an inflation fluid from inflation catheter 48 through inflation valve 50. The inflation fluid can be any biocomplatable fluid, for example, saline, blood, plasma, serum, micronized submucosa, submucosa gel, submucosa strand material or expandable submucosa. The submucosa, may be, for example, small intestinal submucosa.

After inflation of balloon 29, inflation valve 50 is closed and inflation catheter 48 detached from the occlusion device and removed from the vessel. In one embodiment, inflation valve 50 is a twist and close valve that can be closed by a twist of a guidewire. Detachment of inflation catheter 50 can also be achieved by twisting the guidewire.

In certain embodiments, a delivery catheter 42 is a rapid exchange catheter allows exchange from a one catheter to another catheter without the need to replace the catheter guide wire before exchanging the catheters. Such delivery methods are described in U.S. Pat. Nos. 5,690,642, 5,814,061 and 6,371,961, the contents of which are incorporated by reference.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A device comprising:
   a hub extending from a upstream end to a downstream end and along a central axis;
   a plurality of struts attaching to the hub and extending upstream from the hub;
   a plurality of attachment lines each having a first end attaching to the hub; and
   an inflatable balloon positioned downstream of the hub and having an open upstream end and a closed downstream end, wherein a second end of each of the plurality of attachment lines attaches to a perimeter of the open upstream end, wherein the closed downstream end is free to move away and downstream from the hub upon inflation of the balloon and wherein the balloon is impermeable to fluid flow when inflated.

2. The device of claim 1, wherein the struts are movable from a closed configuration wherein the struts extend substantially along the central axis to an open configuration wherein the struts extend radially away from the central axis.

3. The device of claim 1, wherein the plurality of struts comprises at least six struts.

4. The device of claim 1, further comprising a holding mechanism positioned at an upstream end of at least one of the plurality of struts.

5. The device of claim 4, wherein the holding mechanism comprises a hook or a barb.

6. The device of claim 1, wherein the balloon comprises a material selected from the group consisting of a nylon, polyamide, polyolefin, polyester, polyurethane, fluoropolymer, polyethylene, polytetrafluoroethylene (PTFE), polyethyleneterepthalate (PET), polyvinyl chloride, latex, natural rubber, synthetic rubber, elastomer, silicone and mixtures and copolymers thereof.

7. The device of claim 6, wherein the balloon comprises a polyamide.

8. The device of claim 1, wherein the attachment lines are formed from a suture material.

9. The device of claim 1, wherein the attachment lines are formed from a super-elastic nickel-titanium alloy.

10. The device of claim 1, wherein at least a portion of the perimeter of the open upstream end comprises a stiffened portion.

11. The device of claim 10, wherein the stiffened portion assists in the inflation of the balloon.

12. A device comprising:
   a hub extending from a upstream end to a downstream end and along a central axis;
   a plurality of struts attaching to the hub and extending upstream from the hub;
   a holding mechanism positioned at an upstream end of at least one of the plurality of struts;
   a plurality of attachment lines each having a first end attaching to the hub; and
   an inflatable balloon positioned downstream of the hub and having an open upstream end and a closed downstream end, wherein a second end of each of the plurality of attachment lines attaches to a perimeter of the open upstream end, wherein the closed downstream end is free to move away and downstream from the hub upon inflation of the balloon and wherein the balloon is impermeable to fluid flow when inflated.

* * * * *